US00PP27741P3

(12) United States Plant Patent
Byrne et al.

(10) Patent No.: US PP27,741 P3
(45) Date of Patent: Mar. 7, 2017

(54) PEACH TREE NAMED 'FLAT DELIGHT ONE'

(50) Latin Name: *Prunus persica*
Varietal Denomination: Flat Delight One

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 137 days.

(21) Appl. No.: 14/544,521

(22) Filed: Jan. 13, 2015

(65) Prior Publication Data

US 2016/0205834 P1 Jul. 14, 2016

(51) Int. Cl.
*A01H 5/08* (2006.01)

(52) U.S. Cl.
USPC ..... Plt./195

(58) Field of Classification Search
USPC ..... Plt./195, 197
See application file for complete search history.

(56) References Cited

U.S. PATENT DOCUMENTS

PP14,627 P3 * 3/2004 Byrne et al. ..... Plt./197
PP14,629 P3 * 3/2004 Byrne et al. ..... Plt./198
PP26,119 P3 * 11/2015 Byrne et al. ..... Plt./197

OTHER PUBLICATIONS

Burleson Cleburne Times Review Mar. 14, 2014, retrieved on Jul. 14, 2016, retrieved from the Internet at <http://www.cleburnetimesreview.com/community/new-peach-trees-available-at-jcmg-plant-sale/article_807322c2-2ce7-531d-842a-a994a3b1a7b7.html> 3 pp.*

Clemson University—Variety Evaluations June Gold 2001, retrieved on Jul. 13, 2016, retrieved from the Internet at <http://www.clemsonpeach.org/index.php?p=181&e=683> one page.*

Reed New series of peaches to go on sale in 2014, Jan. 1, 2014, The Eagle: Local News, retrieved from the Internet at < http://www.theeagle.com/news/local/new-series-of-peaches-to-go-on-sale-in/article_75f87747-46ae-5782-a079-84ac4628c57d.html> 4 pp.*

The Brooks and Olmo Register of Fruit and Nut Varieties, 3rd Ed., American Society of Horticultural Science Press, Alexandria, VA, 1997, p. 396.

Byrne et al.; 'TexFirst', An early ripening low chill peach for the subtropics; HortScience; 2012; pp. 1803-1804; vol. 47.

* cited by examiner

*Primary Examiner* — June Hwu
(74) *Attorney, Agent, or Firm* — Ramey & Schwaller, LLP

(57) ABSTRACT

Disclosed is a new variety of *Prunus persica* named 'Flat Delight One'. This new variety, which requires 450-500 chilling units of dormancy, is a low-acid, flat (pantao) peach tree of early season maturity, which produces white-fleshed fruit that are firm, attractively colored, and suitable for the local fresh fruit market and home garden use.

4 Drawing Sheets

Latin name of the genus and species of the plant claimed: *Prunus persica.*

Variety denomination: 'Flat Delight One'.

BACKGROUND OF THE INVENTION

Field of the Invention

This invention relates to peach trees referred to as a variety of *Prunus persica* named 'Flat Delight One' 'Flat Delight One', which requires 450-500 chilling units of dormancy, produces an high quality, firm clingstone, low-acid, white-fleshed pantao peach that matures early mid-season.

SUMMARY OF THE INVENTION

The 'Flat Delight One' peach is characterized as to novelty by producing flat shaped, low acid, white-fleshed fruit that ripens in the early mid-season; is considered high quality; and which is firm and has an attractive coloration.

In this regard, the present variety of peach tree bears fruit that are ripe for commercial harvesting and shipment in mid to late May, 4-7 days after 'TexKing' (Byrne and Bacon, U.S. Plant Pat, No. 14,627) and with the medium chill peach 'June Gold' (Brooks, U.S. Plant Pat. No. 1,884) in the medium chill zone of Texas.

Origin of the Variety

The present peach tree was the result of an ongoing Stone Fruit Breeding Program of Texas A & M University, College Station, Brazos County, Tex. To this end, both controlled and hybrid crosses are made each year in order to produce seedling populations from which improved progenies are evaluated and selected.

'Flat Delight One' (selection name, TX3C395LWP) was discovered at the Texas A & M University Horticultural Farm in College Station, Tex. in 2010, and was chosen from a population of seedlings that resulted from seed from a cross between the low chill peach 'TexFirst', the female parent, clingstone yellow-fleshed peach (Byrne and Anderson, U.S. Plant Pat. No. 26,119) and unreleased selection P1, a white-fleshed pantao peach of unknown origin (Ruijuan Ma, personal communication) that ripens mid to late July in Nanjing, China and requires 700 chilling units of dormancy. Resulting seed from this cross were planted in 2007 at the Texas A & M University Horticultural Farm in College Station, Tex. TX3C395LWP was propagated by budding on Nemaguard rootstock and planted in three sites in Texas for further evaluation (Floresville, College Station, Fairfield). Two-year and older trees of the variety were subsequently evaluated during the 2012 and 2013 fruit growing seasons in Texas (Floresville, College Station and Fairfield).

Asexual Reproduction of the Variety

'Flat Delight One' was bud grafted onto virus-free Nemaguard (Brooks and Olmo 1997) peach rootstock in June 2010 at the nursery site in Oakdale, Calif. The variety was subsequently planted at the three experimental orchards in Texas (College Station, Floresville, and Fairfield). Fruit from the resulting propagation has been evaluated during the period from 2012 to 2013 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographic drawings and depicts the plant by the best possible color representation using color photography, wherein.

BOTANICAL DESCRIPTION OF THE VARIETY

Figure 1:
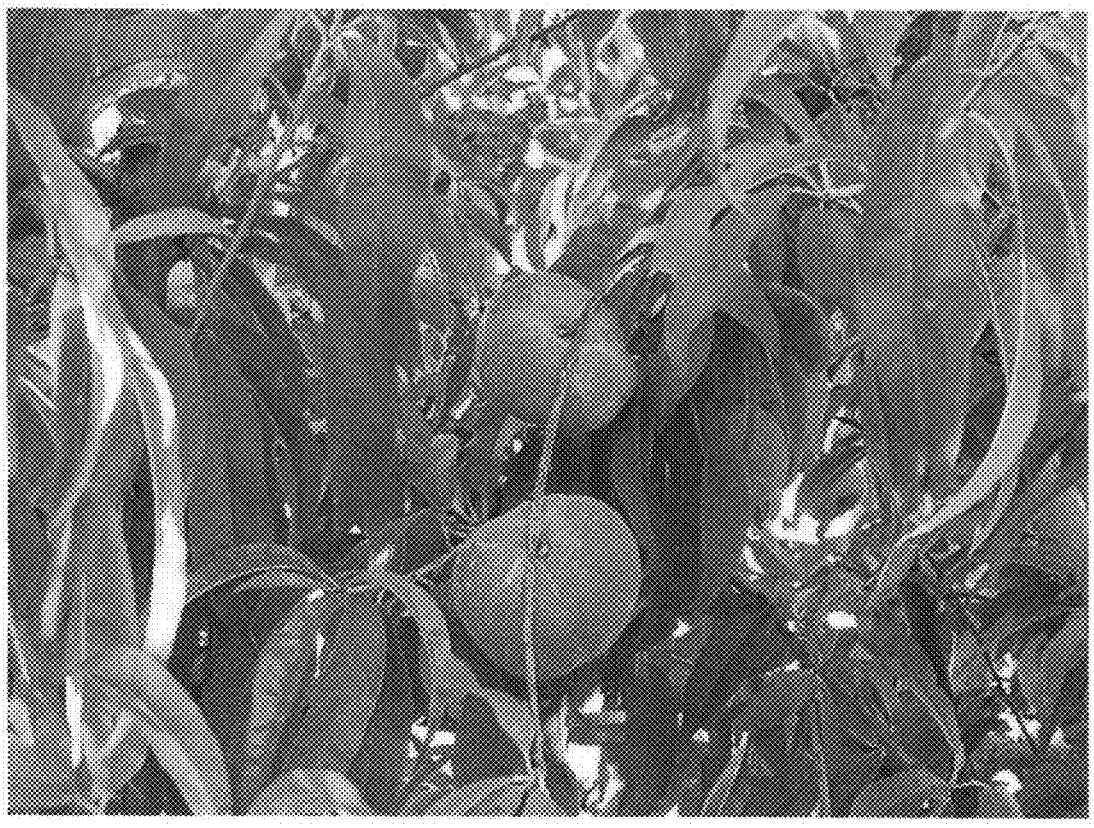
FIG. 1. Fruit of 'Flat Delight One' showing red skin coloration of this white-fleshed pantao peach on a tree. The fruit was produced on a tree in the experimental orchard in College Station, Tex.
Figure 2:
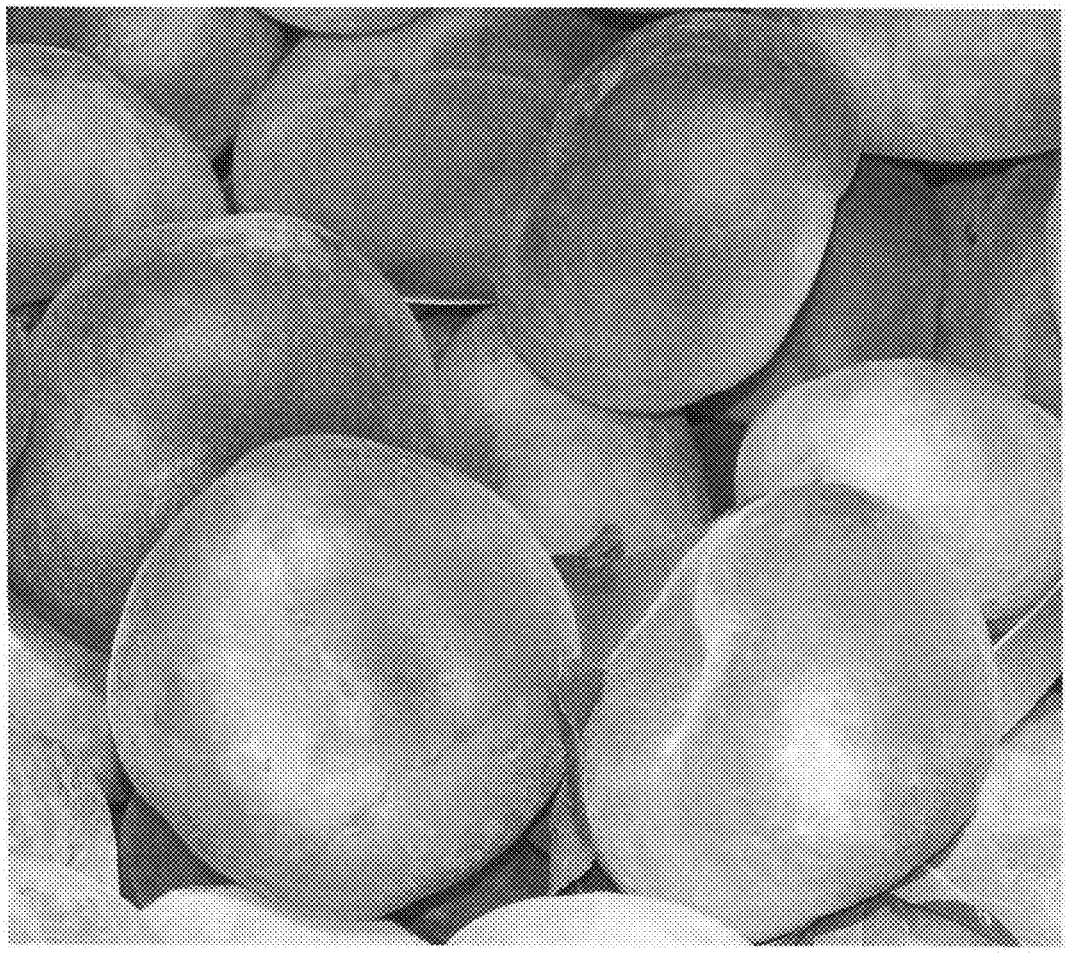
FIG. 2. Color photograph of a ripe 'Flat Delight One' fruit showing round shape with a sealed tip and external coloring. The fruit was harvested in the research plots in College Station, Tex.
Figure 3:
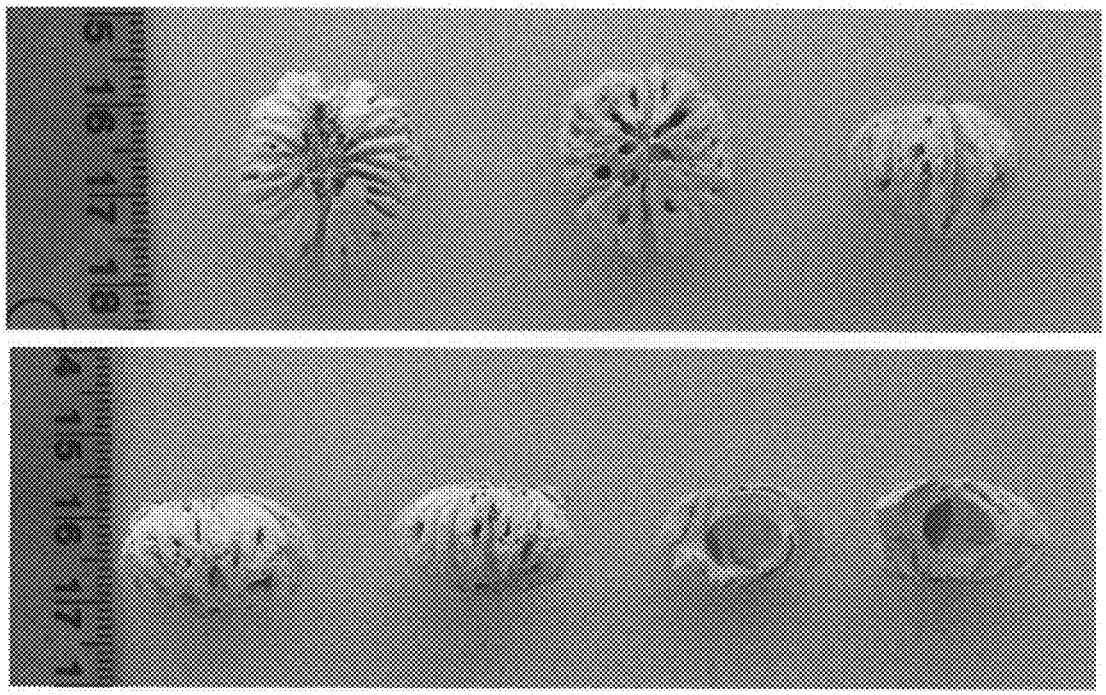
FIG. 3. Color photographs of the endocarp of 'Flat Delight One'. The ruler is demarcated in millimeters.
Figure 4:
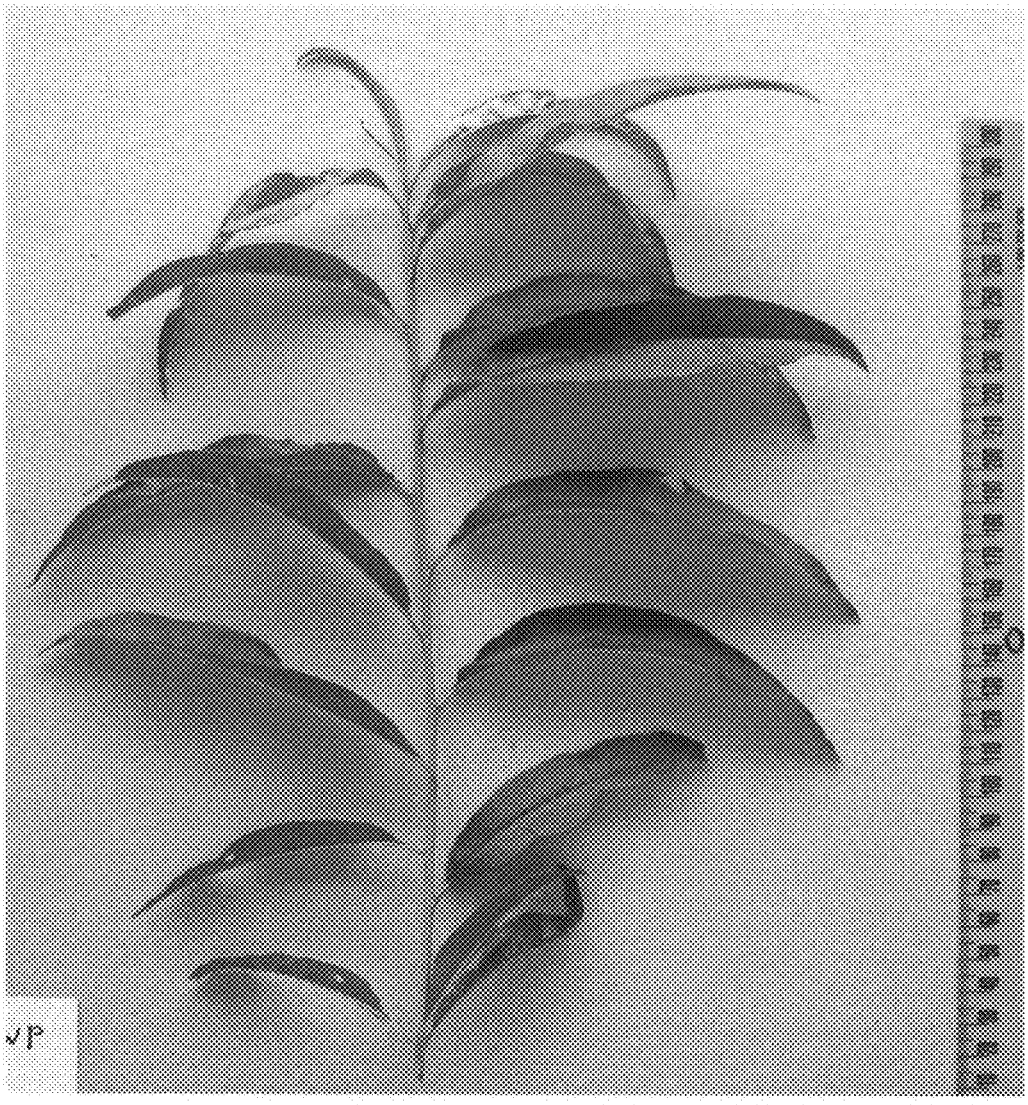
FIG. 4. A stem showing the leaves of the 'Flat Delight One' peach. The ruler is demarcated in millimeters.

Referring more specifically to the pomological details of this new and distinct variety of peach tree, the following has been observed under the ecological conditions prevailing at the experimental orchards in the medium chill zone of Texas. All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars. Observations were done on trees that were three years old.

*Height*.—8 feet (2.44 m) at the end of the 2013 growing season on three year old trees.

*Width*.—10 feet (3.05 m) at the end of the 2013 growing season on three year old trees.

*Vigor*.—High.

*Density*.—Medium to high.

*Productivity*.—Productive. The tree sets an excess of fruit and needs thinning to adjust the fruit load to an appropriate commercial level.

*Shape*.—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth*.—The current season growth for the new variety was approximately 3.3 to 3.5 feet (1.01-1.07 m).

*Regularity of bearing*.—Regular, and considered hardy under typical conditions experienced in the medium chill zone of central Texas (College Station, Fairfield, Terrell, USDA Hardiness Zones 8a and 8b) and in central San Joaquin Valley in California (USDA Hardiness Zone 9b).

Trunk:

*Size*.—Approximately 4.75 inches (12.07 cm) in diameter and 15.75 inches (40.01 cm) in circumference when measured at a distance of approximately 8 inches (20.32 cm) above the soil level, at the end of the 2013 growing season on a three-year old tree.

*Bark texture*.—Considered moderately rough with numerous folds of papery scarf-like skin being present.

*Bark coloration*.—Variable, colors present are 166A of the Greyed-Orange Group and N200B-D of the Brown Group.

Branches:

*Size*.—Considered medium for the variety.

*Thickness*.—Average (about 6.0-9.5 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 6.0 to 8.0 mm in width and were approximately 1.0-2.0 mm in height.

*Current season shoots*.—Surface texture — Substantially glabrous.

*Internode length*.—Approximately 2.5 to 3.0 cm as measured in the middle of a current season stem.

*Color of mature branches*.—The predominant colors are 165A, 166A-B and 177A of the Greyed-Orange Group, N199C of the Grey-Brown Group, and 200B-D and N200C of the Brown Group.

*Current season shoots*.—Color — Light green (144B-C, N144D and 145B of the Yellow-Green Group). The color of new shoot tips is considered a bright and shiny green (mainly the Yellow-Green Groups 144D and 145B).

Leaves:

*Size*.—Considered medium to moderately large for the species. Leaf measurements have been taken from vigorous upright current season growth approximately at mid-shoot.

*Leaf length*.—Approximately 131 to 173 mm.

*Leaf width*.—Approximately 30 to 37 mm.

*Leaf thickness*.—Less than 1 mm.

*Leaf form*.—Lanceolate.

*Leaf tip form*.—Acuminate.

*Leaf upper surface color*.—Green, approximately 137A-C of the Green Group.

*Leaf lower surface color*.—Green, approximately 137B-C and 147B of the Yellow-Green Group.

*Leaf mid-vein color*.—Light green, approximately 145C-D and 149D of the Yellow- Green Group.

*Leaf margins*.—Form — Considered crenate/crenulate. Uniformity — Considered generally uniform.

*Leaf petioles*.—Size — Considered medium long. Length — Approximately 9 to 12 mm. Thickness — Approximately 1 to 2 mm. Color — Pale green (145C-D and 149D of the Yellow-Green Group).

*Leaf glands*.—Size — Approximately 1 mm in height and width. Number — Generally 0-2 per leaf. Type — Reniform. Color — Brown, approximately 165A, 166A and 177A of the Greyed-Orange Groups, plus N199B of the Grey-Brown Group and 200C-D of the Brown Group.

*Leaf stipules*.—Size — Medium to large for the variety. Length — Approximately 6 to 9 mm. Form — Lanceolate. Color — The green stipules are early deciduous. Ratio of wood (leaf) buds to flowering buds — 1 to 2 flower buds per vegetative bud.

Flowers:

*Floral buds*.—General — The floral buds are considered to be medium to medium large in size, conic in form, and slightly appressed relative to the bearing shoot. Color — The bud scales are maroon with green, (approximately Greyed-Yellow Group 160B and Greyed-Purple Groups N186C and 187A-B). The buds are considered hardy under typical conditions found in the medium chill zone of Texas and the central San Joaquin Valley, Calif. Length — Approximately 5 to 8 mm. Blooming Type — Considered relatively early in relation to other peach cultivars grown in the medium chill zone of Texas. Date of full bloom was between February 15th and February 28th during the period between 2011 and 2013. The average bloom was February 23rd during this time period 10-14 days before 'June Gold' (Brooks, U.S. Plant Pat. No. 1,884) and with or a few days after the medium chill peach 'TexKing' (U.S. Plant Pat. No. 14,627).

*Flower type*.—Showy.

*Flower size*.—Flower diameter at full bloom is approximately 30 to 35 mm.

*Bloom quantity*.—Considered abundant.

*Flower bud frequency*.—Normally 1 to 2 per node.

*Petal size*.—General — Considered medium large to large for the species. Width — Approximately 15 to 18 mm. Length — Approximately 20 to 22 mm.

*Petal form*.—Broadly ovate.

*Petal count*.—Nearly always 5.

*Petal color*.—Medium pink when young (Red-Purple Groups N57C-D and 62B-C), becoming darker near the petal claw.

*Petal claw*.—Form — The claw is considered truncate in shape and has a medium-large size when compared to other varieties. Length — Approximately 2 to 3 mm. Width — Approximately 1 mm.

*Petal margins*.—Generally considered variable, from nearly smooth to slightly undulate.

*Petal apex*.—Generally — The petal apices appear emarginate.

*Flower pedicel*.—Length — Considered medium in length with an average length of approximately 2 to 3 mm. Thickness — Considered average, approximately 1 mm. Color — A light green (Green Group 142A-B and Yellow-Green Groups 144B-C and 149B-C).

*Floral nectaries*.—Color — The floral nectaries are yellow in color (Green Yellow Group 1A and Yellow Group 3A-B).

*Hypanthium*.—Surface Texture — Generally glabrous. Color — A purple-red (approximately Red-Purple Groups 61A and 64A-B).

*Sepals*.—Surface Texture — The surface has a short, fine, wooly and a gray-colored texture. Size — Average, and ovate in form. Color — A dull green with red (approximately Yellow-Green Groups 144A, 146C- D and Orange-Red Group N34A).

*Anthers*.—General — Average in size for the species. Color — Yellow-orange (approximately Yellow Group 13A-B, Yellow-Orange Group 15B-C and Orange Group N25A). Pollen Production — Pollen is abundant, and is a golden-yellow color (approximately Yellow Group 13A-B and Yellow-Orange Group 14C).

*Filaments*.—Size — Variable in length, approximately 16 to 23 mm, with the filaments slightly longer than the pistil. Color — White (approximately Green-White Group 157D, Yellow-White Group 158D and Orange-White Group 159D) and darkening with advanced maturity.

*Pistil*.—General — Average in size, but slightly shorter, relative to the general anther height, overall. Length — Approximately 12 to 15 mm, including the ovary. Color — Considered a very light yellow-green when young (approximately Yellow-Green Groups 145C-D, 149D and 150D), and becoming slightly darker with advancing senescence. Surface Texture — The variety has a short, silver white pubescent pistil and ovary (approximately White Group 155A-C and Green-White Group 157D).

Fruit:

*Maturity when described*.—The present variety of fruit is described, as it would be found in its firm ripe condition at full commercial maturity. Under the ecological conditions prevailing in the medium chill of Texas this cultivar is picked from Mid to late May depending on the year and the site of the orchard. The average time of harvest for Fairfield, Tex. was May 23rd which was with 'June Gold'.

*Size*.—General — Medium to medium large for the season and considered uniform.

*Average cheek diameter*.—Approximately 67 to 71 mm.

*Average suture diameter*.—Approximately 65 to 69 mm.

*Average axial diameter*.—Approximately 34 to 39 mm.

*Fruit form*.—Generally considered flat with equal halves. Occasionally the fruit exhibits less symmetry when comparing the suture height with the line opposite the suture. The fruit is generally uniform in symmetry when viewed from the apical aspect.

*Fruit suture*.—Generally, the suture appears as a thin, dark line that extends from the base to the apex, and appears deeper at the apex, forming a shallow basin at the apical point. Some stitching exists along the suture line. Color — Red, approximately 42A of the Red Group. Ventral Surface — Form — Considered depressed.

*Stem cavity*.—Size — Considered moderately shallow for the species. Width — Approximately 8 to 9 mm. Length — Approximately 12 to 15 mm. Depth — Approximately 6 to 8 mm. Form — Considered variable from round to flat.

*Fruit base*.—Flat.

*Fruit apex*.—Flat.

*Fruit stem*.—Length — 9 to 11 mm. Thickness — 3 to 4 mm. Color — Light green, approximately 142B of the Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed. Skin Color — Generally — Variable, with approximately 50-75% of the fruit surface covered with an attractive red blush. Down — Light and short Blush Color — Varying from deep to medium red, approximately 47A and 53A of the Red Group, plus 59A of the Red-Purple Group. Skin Ground Color — Varies from a yellowish-green to medium yellow, approximately 2B, 9D and 10C-D of the Yellow Group.

*Flesh color*.—Light yellow, approximately 8D of the Yellow Group, with small spots of red present (46A and 48A of the Red Group).

*Flesh fibers*.—Present, numerous and lightly colored. These fibers are present throughout the flesh.

*Stone cavity color*.—Ivory to pale yellow, approximately 13D of the Yellow Group and 15D of the Yellow-Orange Group.

*Flesh texture*.—Generally, the flesh is considered firm at commercial maturity.

*Ripening*.—Generally the fruit of the present variety ripens evenly.

*Flavor*.—Considered very sweet flavor.

*Aroma*.—Pleasant and reasonably abundant.

*Eating*.—Generally considered very good to excellent.

Stone:

*Attachment*.—Clingstone at commercial maturity.

*Stone size*.—Generally considered small. Length — Approximately 14 to 15 mm. Width — Approximately 21 to 22 mm. Thickness — Approximately 19 to 20 mm.

*Fibers*.—Generally a few medium length fibers are attached along the entire surface of the stone.

*Stone form*.—Flat

*Stone base*.—Very wide

*Apex shape*.—Very wide

*Stone shape*.—The stone normally flat.

*Stone surface*.—Surface Texture — A mixture of single pits and pit grooves. Ridges — Numerous ridges are present basally, and converge towards the base of the stone. Ventral Edge — Small. Dorsal Edge — Shape — Grooved and having smooth edges.

*Stone color*.—The color of the dry stone is light brown (20C of the Yellow-Orange Group and 165D of the Greyed-Orange Group). The color of the inside surface of the endocarp is primarily 18B-C and 19C of the Yellow-Orange Group.

*Tendency to split*.—Splitting not observed.

*Kernel*.—The kernel does not fills the endocarp at harvest and measures approximately 4-6 mm in thickness, 5-7 mm in width, and 4-5 mm in length. When dried the shriveled kernels measure approximately 1-2 mm in thickness, 6 mm in width, and 3-5 mm in length. The colors of the shriveled kernels are primarily 164A and 165B of the Greyed-Orange Group. The dried seed of 'Flat Delight One' is not viable.

Use: The subject variety, 'Flat Delight One', is considered to be a peach tree of early mid-season maturity, which produces flat, melting flesh, low acid, white-fleshed fruit which are firm, attractively colored, and which are useful for the local fresh market and home garden use.

Keeping quality: Average.

Resistance to insects and disease: It is moderately susceptible to bacterial leaf spot spot [*Xanthomonas campestris* pv. pruni (E. F. Smith) Dye]. No observations were made on susceptability nor resistance to other diseases or insects.

Shipping quality: Average.

Although the new variety of peach tree possesses the described characteristics when grown under the ecological conditions prevailing in the medium chill zone of Texas, it will be understood that variations of the usual magnitude and characteristics incident to the changes in growing conditions, fertilization, pruning, and pest control are to be expected.

REFERENCES

Anon. 2001. R.H.S. Colour Chart. The Royal Hort. Soc., London.

Brooks, R. M. 1958. Double Delight, Earligold, and June Gold peaches. Fruit Var. J. 3:22. U.S. Plant Pat. No. 1,884.

Brooks, R. M. and H. P. Olmo. 1997. Register of New Fruit and Nut Varieties. 3rd Edition. American Society of Horticultural Science Press, Alexandria, Va.

Byrne, D. H. and N. Anderson. 2013. TexFirst, an Early-ripening, low chill peach for the subtropics. HortScience 47(2):1803-1804. U.S. Plant Pat. No. 26,119.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

We claim:

1. A new and distinct *Prunus persica* tree, substantially as illustrated and described herein.

* * * * *